(12) United States Patent
Panseri et al.

(10) Patent No.: US 6,794,538 B2
(45) Date of Patent: Sep. 21, 2004

(54) PROCESS FOR THE PREPARATION OF ETHERS DERIVING FROM HYDROXYBENZOIC ACIDS

(75) Inventors: Pietro Panseri, Bergamo (IT); Vittorio Messori, Milan (IT); Patrizia Mangini, Vimercate-Milan (IT)

(73) Assignee: Borregaard Italia S.p.A., Milan (IT)

( * ) Notice: Subject to any disclaimer, the term of this patent is extended or adjusted under 35 U.S.C. 154(b) by 59 days.

(21) Appl. No.: 10/130,307
(22) PCT Filed: Nov. 29, 2000
(86) PCT No.: PCT/EP00/12005
§ 371 (c)(1),
(2), (4) Date: May 31, 2002
(87) PCT Pub. No.: WO01/40158
PCT Pub. Date: Jun. 7, 2001

(65) Prior Publication Data
US 2003/0045748 A1 Mar. 6, 2003

(30) Foreign Application Priority Data
Dec. 3, 1999 (IT) .......................... MI99A2534

(51) Int. Cl.[7] .............................. C07C 65/00
(52) U.S. Cl. ..................... 562/473; 562/474
(58) Field of Search .................. 562/473, 474

(56) References Cited
U.S. PATENT DOCUMENTS 3,316,296 A    4/1967  Keisuke
3,855,285 A  * 12/1974 Holland ..................... 562/432
4,161,611 A  *  7/1979 Kim ........................... 562/474

FOREIGN PATENT DOCUMENTS

JP          07179433       *  7/1995

OTHER PUBLICATIONS

Zh. Org. Khin, 1987 23(3), pp 667–668.*
PCT International Preliminary Examination Report for PCT EP00/12005.*
Chemical Abstracts, vol. 107, No. 23, 1987, Columbus, Ohio, US; abstract No. 217198h, Kotlyar, S.A.; Klimova, E.I.; Lukyaneko, N.G.: "Crown–ether catalyzed alkylation of hydroxybenzoic acids" p. 546.

* cited by examiner

*Primary Examiner*—Paul J. Killos
*Assistant Examiner*—Hector M. Reyes
(74) *Attorney, Agent, or Firm*—Oblon, Spivak, McClelland, Maier & Neustadt, P.C.

(57) ABSTRACT

Process for the preparation of ethers of hydroxybenzoic acid having general formula (I), which comprises reacting a hydroxybenzoic acid, optionally substituted, with a halide $XR_1$, wherein X is a halogen such as chlorine, in a basic environment and in an aqueous or aqueous/organic biphasic solvent.

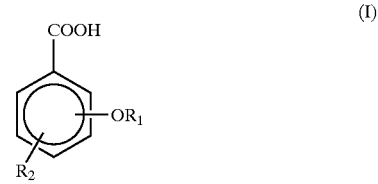

6 Claims, No Drawings

PROCESS FOR THE PREPARATION OF ETHERS DERIVING FROM HYDROXYBENZOIC ACIDS

The present invention relates to a process for the preparation of ethers deriving from hydroxybenzoic acids. These products are particularly useful as intermediates for pharmaceutical syntheses, in agrarian chemistry, in dyes, fragrances, pharmaceutical solutions for dental cements and as adhesive components.

More specifically, the present invention relates to a process for the production of o-ethoxybenzoic acid (2-EBA) used in particular as an intermediate for pharmaceutical syntheses.

Preparation methods of ethers of hydroxybenzoic acids are known in literature. For example, in Zh. Org. Khim., vol. 23, Nr. 3, pages 667–668, the preparation is described of alkyl ethers of hydroxybenzoic acid starting from an aqueous solution of potassium hydroxide, containing o-hydroxybenzoic acid, and from an alkyl halide. The reaction, catalyzed by crown-ethers, also produces high quantities of ether with the esterified carboxylic function. This ether-ester must be treated in a second phase to saponify the esterified function by means of hydrolysis.

With the aim of overcoming this drawback, a synthesis method alternative to the previous one was proposed in the patent U.S. Pat. No. 5,344,968, which comprises the reaction between a chlorobenzoic acid and a $C_1$–$C_5$ alkyl alcohol in the presence of a catalytic system consisting of a copper salt and an alkyl amine. Although characterized by a better selectivity, with respect to the method described above, the process of patent U.S. Pat. No. 5,344,968 still requires the use of a complex catalytic system which, at the end of the reaction, must be separated from the end-product.

U.S. Pat. No. 4,161,611 teaches the preparation of a methyl ether of 2-hydroxy3,6-dichlorobenzoic acid with methyl chloride in water and sodium hydroxide, the pH being maintained during the reaction in the range of 10–12 by the periodic addition of NaOH.

The Applicant has now found that it is possible to obtain alkyl ethers of hydroxybenzoic acids in a single passage by reacting salicylic acid with an alkyl chloride, in the presence of a base, without the formation of an ether-ester. More specifically, operating according to the process object of the present invention, it is possible to obtain alkoxybenzoic acid directly with good yields and a high selectivity by reacting, in water, an alkaline salt of salicylic acid with an alkyl chloride and an alkaline base fed simultaneously but so as to maintain a slight excess of alkaline base in reaction, according to the following reaction scheme:

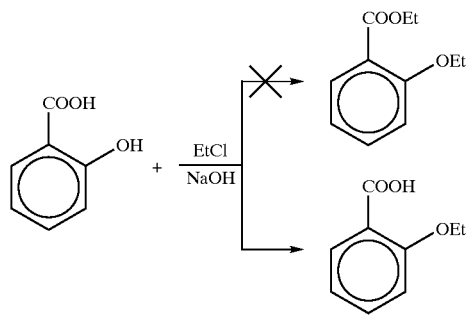

Operating according to this process, the following advantages are obtained with respect to the known art:

use of an economic reagent, such as alkyl chloride, which makes the process competitive also from an industrial point of view;

use of an economic and simple solvent such as water operating in a single aqueous phase;

possibility of also carrying out the reaction in a mixed water/non-miscible solvent (for example toluene) system, thus obtaining a reduction in the reaction pressure;

elimination of reaction by-products such as alkyl esters of etherified salicylic acid, and the consequent elimination of subsequent hydrolysis steps of said ether-esters to obtain the corresponding ethers only.

An object of the present invention therefore relates to a process for the preparation of ethers of hydroxybenzoic acid having general formula (I):

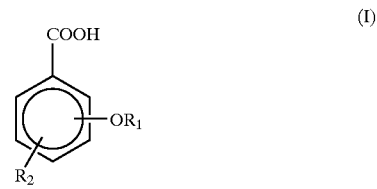

(I)

wherein $R_1$ represents a linear or branched $C_1$–$C_6$ alkyl group or an alkylaromatic group wherein the alkyl group contains from 1 to 4 carbon atoms and wherein $R_1$ represents a hydrogen atom or a $C_1$–$C_4$ alkoxy, phenoxy, benzyloxy group, or a $C_1$–$C_4$ alkyl radical, a $C_2$–$C_4$ alkenyl radical, a —$COCH_3$ or Y—CHO acetyl radical, wherein Y represents a simple bond or a $C_1$–$C_4$ alkyl radical, or it represents an —$NO_2$ or —$NR_3R_4$ group wherein $R_3R_4$, the same or different, are selected from a hydrogen atom or a $C_1$–$C_4$ alkyl radical, which comprises reacting a hydroxybenzoic acid, optionally substituted, with an $XR_1$ halide, wherein X is a halogen such as chlorine, in a basic environment and in an aqueous or aqueous/organic biphasic solvent.

According to the present invention, the preferred but non-limiting compound is that having general formula (I), wherein $R_1$ is an ethyl radical in ortho position with respect to the carboxylic group and wherein $R_2$ represents a hydrogen atom.

The synthesis reaction, which can be carried out by feeding the reagents either in continuous or batchwise, but preferably in continuous, takes place between the hydroxybenzoic acid optionally substituted, preferably salicylic acid, and an alkyl halide, preferably ethyl chloride, in the presence of a base in order to fix the halogen which is released during the reaction in aqueous solvent. The feeding of the reagents is generally carried out in continuous feeding the base in advance with respect to the ethyl chloride.

Preferred bases are aqueous sodium or potassium hydroxides. Organic bases such as trialkylamines can also be used, which block the hydrochloric acid in the hydrochloride form of the amine. Sodium hydroxide used with molar ratios alkyl halide/NaOH ranging from 1/1 to 1/3, preferably equal to 1/5, is particularly preferred. The reaction is carried out in an autoclave at a pressure ranging from 1 to 15 atm and at a temperature ranging from 80° C. to 160° C., preferably from 110° C. to 130° C.

To favour the conversion of the hydroxybenzoic acid, it is preferable to use an excess of alkyl halide with respect to the aromatic substrate. The molar ratios hydroxybenzoic acid/alkyl halide range from 1/1.5 to 1/4, preferably from 1/2 to 1/2.5.

When the reaction solvent is water alone, this is used in such a quantity as to have a weight ratio hydroxybenzoic acid/water, at the end of the feeding, ranging from 1/2 to 1/6, preferably from 1/3 to 1/4. When the water is mixed with a non-miscible organic solvent, for example toluene or xylenes, the latter is present in a quantity ranging from 5 to 50% by volume with respect to the total water+solvent volume.

Some illustrative but non-limiting examples are provided for a better understanding of the present invention.

EXAMPLE 1

69.1 g (0.5 moles) of salicylic acid suspended in 83 g of demineralized water are salified with 69.1 g (0.52 moles) of NaOH at 30% in a 1 liter open autoclave. After closing the autoclave, 80.6 g (1.25 moles) of ethyl chloride and 192 g (1.44 moles) of NaOH at 30% are charged separately but simultaneously in 6 h under strict pressure control. At the end of the feeding, the mixture is left for 2 h at a thermostat-regulated temperature (T=120° C.) until a stable pressure indication is obtained.

The reaction mixture at the end of the synthesis is acidified to pH 1.5–2 with HCL 20% (126.3 g) and extracted with methylene chloride (130 g).

After distillation of the solvent, 70.8 g (0.426 moles) of 2-EBA and 8.6 g (0.062 moles) of non-reacted salicylic acid are recovered, equal to a conversion of 87.6% and a selectivity to 2-EBA of 97.2%.

EXAMPLE 2

The same procedure is adopted as described in example 1, adding, apart from water, an equal volume quantity of toluene (83 cm³) in the autoclave.

At the end of the synthesis, the reaction mixture consists of two separate phases, a toluene phase which is put aside and an aqueous phase which is acidified to pH 1.5–2 with HCl at 20% (120.8 g). This is extracted with toluene (55 g).

After distillation of the joined toluene phases, 71.0 g (0.43 moles) of 2-ERA and 8.1 g (0.059 moles) of non-reacted salicylic acid are recovered, equal to a conversion of 88.3% and a selectivity to 2-EBA of 96.7%.

EXAMPLE 3

The same procedure is adopted as described in example 2, varying only the quantity of ethyl chloride used (114.5 g=1.775 moles) and the corresponding NaOH (272 g=2.04 moles).

After distillation of the solvent, 73.1 g (0.44 moles) of 2-EBA and 6.35 g (0.046 moles) of non-reacted salicylic acid are recovered, equal to a conversion of 90.8% and a selectivity to 2-EBA of 96.8%.

EXAMPLE 14

The same procedure is adopted as described in example 2, varying only the quantity of ethyl chloride used (71.0 g=1.10 moles) and the corresponding NaOH (169 g=1.267 moles).

After distillation of the solvent, 63.7 g (0.383 moles) of 2-EBA and 11.3 g (0.08 moles) of non-reacted salicylic acid are recovered, equal to a conversion of 83.6% and a selectivity to 2-EBA of 91.6%.

EXAMPLE 5

The same procedure is adopted as described in example 2, varying only the reaction temperature from 120° C. to 130° C.

After distillation of the solvent, 69.1 g (0.41 moles) of 2-ERA and 8.15 g (0.059 moles) of non-reacted salicylic acid are recovered, equal to a conversion of 88.2% and a selectivity to 2-EBA of 94.2%.

EXAMPLE 6

The same procedure is adopted as described in example 2, varying only the reaction temperature from 120° C. to 100° C.

After distillation of the solvent, 60.4 g (0.36 moles) of 2-EBA and 13.6 g (0.098 moles) of non-reacted salicylic acid are recovered, equal to a conversion of 80.3% and a selectivity to 2-EBA of 90.5%.

What is claimed is:

1. A process for the preparation of one or more ethers of hydroxybenzoic acid of formula (I):

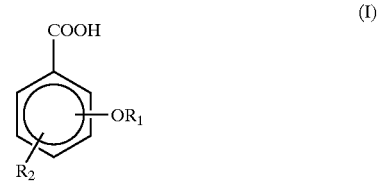

wherein $R_1$ represents a linear or branched $C_1$–$C_8$ alkyl group or an alkylaromatic group wherein the alkyl group contains from 1 to 4 carbon atoms and wherein $R_2$ represents a hydrogen atom or a $C_1$–$C_4$ alkoxy, phenoxy, benzyloxy group, or a $C_1$–$C_4$ alkyl radical, a $C_2$–$C_4$ alkenyl radical, a —$COCH_3$ or Y—CHO acetyl radical, wherein Y represents a single bond or a $C_1$–$C_4$ alkyl radical, or it represents an —$NO_2$ or —$NR_3R_4$ group wherein $R_3$ and $R_4$ may be the same or different, and are selected from the group consisting of a hydrogen atom or a $C_1$–$C_4$ alkyl radical, said process comprising:

reacting continuously at a pressure ranging from 0.1 to 1.52 MPa, a hydroxybenzoic acid, optionally substituted, with an $XR_1$ halide, wherein X is a halogen in a basic environment and in an aqueous or aqueous/organic biphasic solvent, in the presence of NaOH with reaction molar ratios alkyl halide/NaOH ranging from 1/1 to 1/3.

2. The process according to claim 1, wherein $R_1$ is an ethyl radical in ortho position with respect to the carboxyl group and $R_2$ represents a hydrogen atom.

3. The process according claim 1, wherein the reaction molar ratios hydroxybenzoic acid/alkyl halide range from 1/1.5 to 1/4.

4. The process according to claim 1, wherein the reaction is carried out at a temperature ranging from 80° C. to 160° C.

5. The process according to claim 1, wherein the solvent is water and wherein the weight ratio hydroxybenzoic acid/water, when the reagents have been charged, ranges from 1/2 to 1.6.

6. The process of claim 1, wherein the halogen is chlorine.

* * * * *